US008459522B2

(12) United States Patent
Marczyk

(10) Patent No.: US 8,459,522 B2
(45) Date of Patent: *Jun. 11, 2013

(54) POWERED SURGICAL STAPLING DEVICE

(75) Inventor: Stanislaw Marczyk, Stratford, CT (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/545,017

(22) Filed: Jul. 10, 2012

(65) Prior Publication Data

US 2012/0298720 A1 Nov. 29, 2012

Related U.S. Application Data

(63) Continuation of application No. 13/213,332, filed on Aug. 19, 2011, now Pat. No. 8,240,536, which is a continuation of application No. 12/635,924, filed on Dec. 11, 2009, now Pat. No. 8,020,742, which is a continuation of application No. 12/177,954, filed on Jul. 23, 2008, now Pat. No. 7,637,409, which is a continuation of application No. 11/724,744, filed on Mar. 15, 2007, now Pat. No. 7,422,136.

(51) Int. Cl.
*A61B 17/068* (2006.01)
(52) U.S. Cl.
USPC ....... 227/175.1; 227/19; 227/175.2; 606/139; 606/219
(58) Field of Classification Search
USPC 227/19, 176.1, 175.1, 180.1, 175.2; 606/139, 606/219, 151, 153
See application file for complete search history.

(56) References Cited

U.S. PATENT DOCUMENTS

| 4,331,277 | A | 5/1982 | Green |
| 4,606,343 | A | 8/1986 | Conta |
| 4,644,950 | A | 2/1987 | Valli |
| 5,312,023 | A | 5/1994 | Green |
| 5,326,013 | A | 7/1994 | Green |
| 5,350,355 | A | 9/1994 | Sklar |
| 5,383,880 | A | 1/1995 | Hooven |
| 5,389,098 | A | 2/1995 | Tsuruta |
| 5,467,911 | A | 11/1995 | Tsuruta |

(Continued)

FOREIGN PATENT DOCUMENTS

| EP | 1728475 A | 12/2006 |
| EP | 1813203 A | 8/2007 |
| WO | WO2004/032760 A | 4/2004 |

OTHER PUBLICATIONS

European Search Report for corresponding EP08250823 date of completion is Jun. 27, 2008 (7 pgs).

(Continued)

*Primary Examiner* — Scott A. Smith

(57) ABSTRACT

A medical instrument having a tool assembly attachable to a distal end of the medical instrument is disclosed. The tool assembly includes a pair of opposing tissue engaging surfaces for clamping tissue therebetween. The medical instrument also includes a housing having a fixed handle and a movable handle mounted to the housing and selectively movable relative to the fixed handle from a first position in spaced relation relative to the fixed handle to a second position closer to the fixed handle to actuate the clamping of tissue. The instrument further includes a selectively activatable drive assembly including a power source and a motor which is operatively coupled to the movable handle, wherein upon actuation the motor actuates the pair of opposing tissue engaging surfaces.

16 Claims, 3 Drawing Sheets

U.S. PATENT DOCUMENTS

| | | | |
|---|---|---|---|
| 5,518,163 A | 5/1996 | Hooven | |
| 5,518,164 A | 5/1996 | Hooven | |
| 5,529,235 A | 6/1996 | Boiarski et al. | |
| 5,535,937 A | 7/1996 | Boiarski et al. | |
| 5,653,374 A | 8/1997 | Young | |
| 5,667,517 A | 9/1997 | Hooven | |
| 5,779,130 A | 7/1998 | Alesi | |
| 5,782,397 A | 7/1998 | Koukline | |
| 5,810,811 A | 9/1998 | Yates et al. | |
| 5,954,259 A | 9/1999 | Viola | |
| 6,004,335 A | 12/1999 | Vaitekunas et al. | |
| 6,119,913 A | 9/2000 | Adams et al. | |
| 6,461,372 B1 | 10/2002 | Jensen | |
| 6,533,157 B1 | 3/2003 | Whitman | |
| 6,699,177 B1 | 3/2004 | Wang et al. | |
| 6,716,233 B1 | 4/2004 | Whitman | |
| 6,830,174 B2 | 12/2004 | Hillstead et al. | |
| 6,846,307 B2 | 1/2005 | Whitman | |
| 6,846,308 B2 | 1/2005 | Whitman | |
| 6,846,309 B2 | 1/2005 | Whitman | |
| 6,849,071 B2 | 2/2005 | Whitman | |
| 6,981,941 B2 | 1/2006 | Whitman et al. | |
| 7,023,159 B2 | 4/2006 | Gorti et al. | |
| 7,246,734 B2 | 7/2007 | Shelton, IV | |
| 7,422,136 B1 | 9/2008 | Marczyk | |
| 7,464,847 B2 | 12/2008 | Viola et al. | |
| 7,568,603 B2 | 8/2009 | Shelton et al. | |
| 7,637,409 B2 | 12/2009 | Marczyk | |
| 7,717,312 B2 | 5/2010 | Beetel | |
| 7,770,775 B2 * | 8/2010 | Shelton et al. | 227/178.1 |
| 8,020,742 B2 | 9/2011 | Marczyk | |
| 8,240,536 B2 * | 8/2012 | Marczyk | 227/175.1 |
| 2006/0278680 A1 | 12/2006 | Viola et al. | |

OTHER PUBLICATIONS

European Search Report for corresponding EP10194381 date of completion is Apr. 15, 2011 (7 pgs).

* cited by examiner

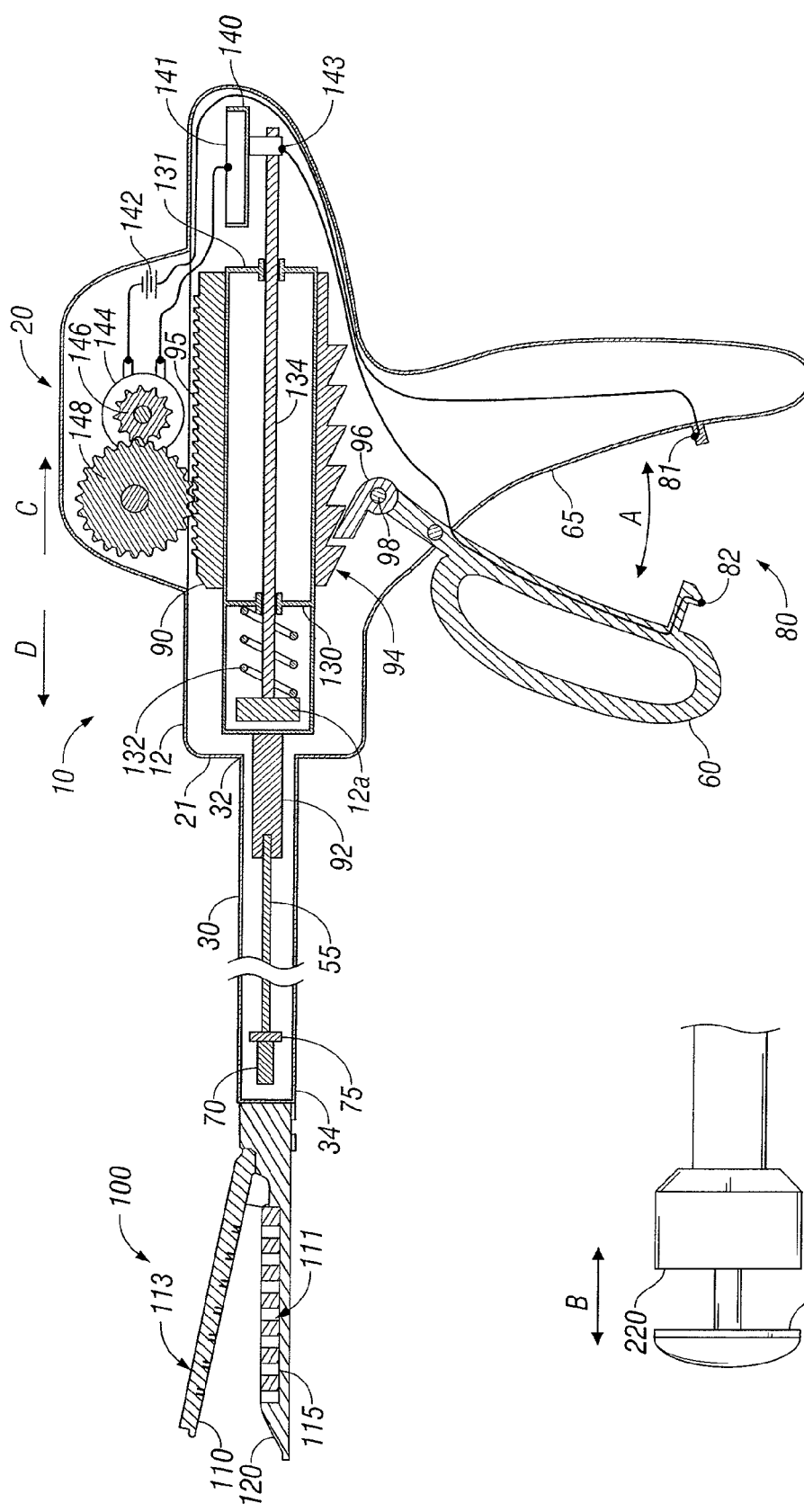
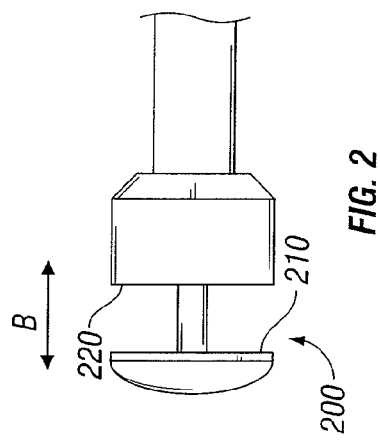
FIG. 1
FIG. 2

POWERED SURGICAL STAPLING DEVICE

CROSS REFERENCE TO RELATED APPLICATIONS

The present application is a continuation of U.S. Ser. No. 13/213,332, filed Aug. 19, 2011, now U.S. Pat. No. 8,240,536, which is a continuation of U.S. application Ser. No. 12/635,924, filed Dec. 9, 2009, now U.S. Pat. No. 8,020,742, which is a continuation of U.S. application Ser. No. 12/177,954 filed Jul. 23, 2008, now U.S. Pat. No. 7,637,409, which is a continuation of U.S. patent application Ser. No. 11/724,744 filed on Mar. 15, 2007, now U.S. Pat. No. 7,422,136, by Stanislaw Marczyk. The disclosures of which are hereby incorporated by reference in its entirety.

BACKGROUND

1. Technical Field

The present disclosure relates to a surgical stapler for implanting mechanical surgical fasteners into the tissue of a patient, and, in particular, to a surgical stapler which is powered by a motor for firing surgical fasteners into tissue.

2. Background of Related Art

Current known devices can typically require 10-60 pounds of manual hand force to clamp tissue and deploy and form surgical fasteners in tissue which, over repeated use, can cause a surgeon's hand to become fatigued.

Gas powered pneumatic staplers which implant surgical fasteners into tissue are known in the art. Certain of these instruments utilize a pressurized gas supply which connects to a trigger mechanism by way of an intricate series of hoses and actuators. The trigger mechanism, when depressed, simply releases pressurized gas to implant a fastener into tissue.

Motor-powered surgical staplers are also known and are disclosed in U.S. Pat. No. 5,383,880 to Hooven and U.S. Pat. No. 6,716,233 to Whitman. The '880 and the '233 patents disclose powered surgical staplers including motors which activate staple firing mechanisms. In particular, the '880 patent discloses a powered stapler wherein the power of the motor is automatically controlled based on various types of sensor data (e.g., tissue thickness). The '233 patent teaches a powered stapler that is automatically controlled as a function of sensor data. However, both of these references only provide for limited user control of the stapling process. The '880 and '233 patents provide the user with the option of toggling a single switch and/or button to actuate the powered stapler which then automatically controls the motor and applies corresponding torque to the stapler's firing mechanisms. Consequently, in these references, the user only controls activation and deactivation of the device and the device does not provide any tactile feedback.

It would be desirable to provide a low cost motor powered stapler that provides the needed energy required to fire the instrument to form a series of surgical fasteners into and through tissue. It would also be desirable to provide an ergonomically advanced surgical stapler which reduces fatigue during repeated use and provides the surgeon with more tactile feedback during activation of the stapler. It would further be desirable to provide a powered stapler which provides the user with tactile feedback allowing to user to vary the force applied by the motor on the stapling and/or clamping mechanisms.

SUMMARY

According to one aspect of the present disclosure, a medical instrument having a tool assembly attachable to a distal end of the medical instrument is disclosed. The tool assembly includes a pair of opposing tissue engaging surfaces for clamping tissue therebetween. The medical instrument also includes a housing having a fixed handle and a movable handle mounted to the housing and selectively movable relative to the fixed handle from a first position in spaced relation relative to the fixed handle to a second position closer to the fixed handle to actuate the clamping of tissue. The instrument further includes a selectively activatable drive assembly including a power source and a motor which is operatively coupled to the movable handle, wherein upon actuation the motor actuates the pair of opposing tissue engaging surfaces. The drive assembly also includes a controller configured to variably control the rate at which the motor actuates the pair of opposing tissue engaging surfaces in response to the force exerted on the movable handle.

According to another aspect of the present disclosure A medical instrument is disclosed. The medical instrument includes a tool assembly attachable to a distal end of the medical instrument, the tool assembly including a pair of opposing tissue engaging surfaces. The instrument also includes a selectively activatable drive assembly including a motor which is operatively coupled to a movable handle, wherein upon actuation the motor actuates the pair of opposing tissue engaging surfaces. The selectively activatable drive assembly also includes a controller configured to variably control the rate at which the motor actuates the pair of opposing tissue engaging surfaces in response to the force exerted on the movable handle.

BRIEF DESCRIPTION OF THE DRAWINGS

Various embodiments of the subject instrument are described herein with reference to the drawings wherein:

FIG. 1 is a schematic, side view with portions broken away of a surgical stapler according to the present disclosure having a motor-powered drive assembly for forming fasteners;

FIG. 2 is a schematic, side view with portions broken away of an alternate embodiment of a tool assembly for use with the stapler of FIG. 1.

DETAILED DESCRIPTION

Figure 3:
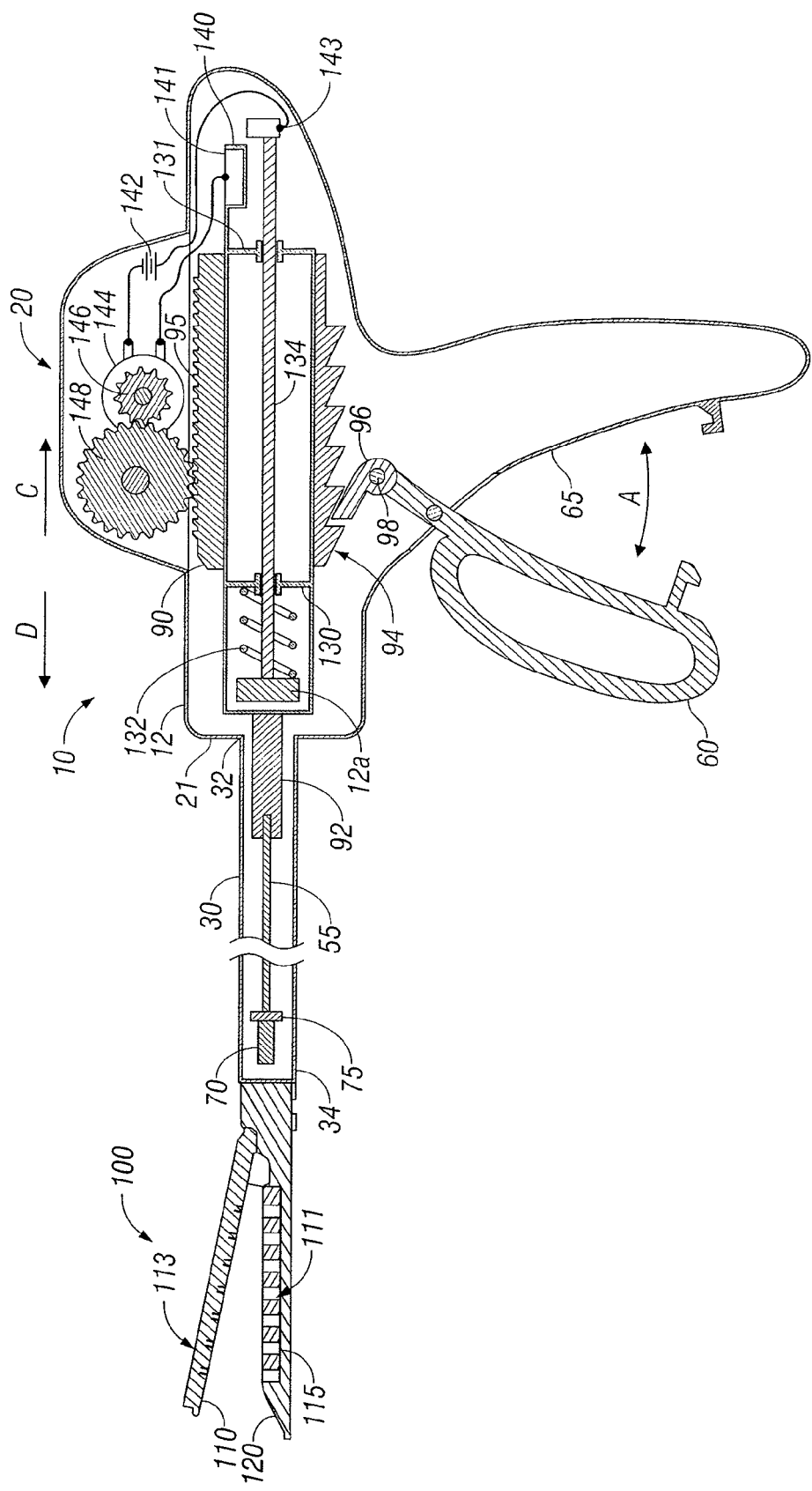
FIG. 3 is a schematic, side view with portions broken away of a surgical stapler according to an embodiment of the present disclosure.

Referring initially to the embodiment disclosed in FIGS. 1 and 2, a surgical stapler 10 is shown having a motor-powered drive assembly here shown as including a drive assembly 20. It is envisioned that the presently disclosed drive assembly 20 can be utilized with any type of known surgical stapler. As such, a general surgical stapler 10 is schematically depicted in the drawings and described herein. For example, stapler 10 includes a housing 12 having an elongated member or shaft 30 attached thereto. Shaft 30 includes a proximal end 32 which attaches to a distal end 21 of the housing 12 and a distal end 34 which operatively couples to a tool assembly such as an end effector 100 or a tool assembly 200. The end effector 100 depicted in FIG. 1 is a conventional longitudinal stapler having opposing tissue contacting surfaces 110 and 120. The contact surface 110 acts as an anvil assembly 113 and the contact surface 120 includes a cartridge assembly 111 having a plurality of surgical fasteners 115. During operation, as the contact surfaces 110 and 120 are closed about tissue, the surgical fasteners 115 are fired from the cartridge assembly 111, through tissue, and the surgical fasteners are deformed by the anvil assembly of the contact surface 110 as discussed in more detail below.

The tool assembly 200 depicted in FIG. 2 is that of a conventional circular stapler (not shown) having opposing tissue contacting surfaces 210 and 220, wherein the contacting surface 210 is formed on the anvil assembly and the contact surface 220 is formed on the cartridge assembly. For the purposes herein, stapler 10 will be described as having tool assembly 100 attached to distal end 34 of an elongate shaft.

Housing 12 includes a fixed handle 65 which is generally in the form of a pistol grip to enhance manipulation of the stapler 10 as needed during surgery. Stapler 10 also includes a movable handle 60 which is movable relative to fixed handle 65 (in the direction "A") to actuate opposing tissue contacting surfaces 110 and 120 of tool assembly 100 to manipulate, grasp fasten and cut tissue. The proximal end of shaft 30 is integrally associated with, mounted to, or selectively attachable to housing 12. One or more actuating assemblies are incorporated within housing 12 and may include manual, robotic or computer operated systems. The actuating assembly may comprise that of a known open or endoscopic surgical stapler. Many types of mechanical actuators and handle mechanisms are known which are configurable to communicate with and actuate the functions of tool assembly 100. Mechanical actuators and handle mechanisms are disclosed in U.S. Pat. Nos. 5,318,221, 5,762,256 and 5,865,361, the disclosures of which are hereby incorporated by reference herein.

As best seen in FIG. 1, a staple deformation or staple firing mechanism 70 (e.g., firing piston) and knife assembly 75 may also be included in distal end 34 of the shaft 30 and/or included with tool assembly 100. It is contemplated that the same or separate actuating mechanisms may be employed to drive staple firing mechanism 70 and knife assembly 75. The movable handle 60 cooperates with tool assembly 100 to grasp tissue, as is known in the art. The movable handle 60 also actuates the drive assembly 20 which drives the staple firing mechanism 70 and/or the knife assembly 75 through tissue. The staple firing mechanism 70 may be configured as a longitudinally movable member or beam that pushes an actuation sled through cartridge assembly 111 to deploy staples against the anvil assembly 110, as is known in the art. Such a mechanism is disclosed in U.S. Patent Application Publication No. 2004/0232201, the disclosure of which is hereby incorporated by reference herein, in its entirety.

FIG. 1 shows one embodiment of a stapler 10 which includes the drive assembly 20 housed within surgical stapler 10 to actuate a firing shaft 55 which, in turn, cooperates with tool assembly 100 to clamp tissue between tissue engaging surfaces 110 and 120 and to drive a plurality of surgical fasteners 115. For example, as disclosed in U.S. Patent Publication No. 2004/0232201, the drive beam may include a member, such as a cam roller, for engaging a cam surface of the anvil assembly to approximate the cartridge assembly and anvil assembly and to clamp tissue therebetween. The same drive beam may also be used to deploy the staples from the cartridge assembly. The disclosure of U.S. Patent Application Publication No. 2004/0232201 is hereby incorporated by reference herein. Surgical stapler 10 is preferably, as shown, designed for one-handed operation by the user and requires minimal pulling force of the movable handle 60 to deform the surgical fasteners 115 through tissue. In other words, stapler 10 is designed such that drive assembly 20 actuates and controls the high-force portion of the activation sequence (i.e., the so-called "firing stroke") thus alleviating user fatigue and allowing simple, consistent and repeated use of the stapler during surgery.

The drive assembly 20 includes a coupling member 90 operatively coupled to a shaft connector 92 which is coupled to the firing shaft 55, such that longitudinal movement of the coupling member 90 in the direction "D" is translated to the firing shaft 55. The coupling member 90 includes a ratchet track 94 having one or more teeth interfacing with a pawl 96 allowing for unidirectional motion. The pawl 96 is rotatively coupled to the movable handle 60 via a pin 98, such that when the movable handle 60 is pulled toward the handle 65, the pawl 98 engages one of the teeth of the ratchet track 94 and pushes the coupling member 90 in the distal direction "D." The staple firing mechanism 70 is advanced by the distal movement of the coupling member 90 and firing shaft 55. The staple firing mechanism 70 engages the anvil assembly 113 and cartridge assembly 111 to clamp tissue therebetween. Further actuation of the staple firing mechanism deploys staples from the staple cartridge assembly 111 and deforms the staples against the anvil assembly 113.

The coupling member 90 includes a lumen defined therein having supporting walls 130 and 131. The supporting wall 130 along with the shaft connector 92 encloses a spring 32 or another compression mechanism. The spring 32 applies pressure onto supporting wall 130 which in turn pushes the coupling member 90 in the proximal direction "C." The pressure on the coupling member 90 also moves apart the movable handle 60 away from the fixed handle 65, keeping the movable handle 60 in an unactuated position (e.g., first position).

The drive assembly 20 includes an electric DC motor 144 connected to a power source 142 (e.g., a battery). A variable resistor 140 and a switch 80 are connected in series with the DC motor 144 and the power source 142. The switch 80 is open when the movable handle 60 is in the first position and is closed when then movable handle 60 is pulled in the proximal direction into the second position actuating the coupling member 90. In particular, a contact 82 disposed on the movable handle 60 contacts a contact 81 disposed on the fixed handle 65. Once the contacts 81 and 82 are touching, the switch 80 is closed and the DC motor 144 is activated. It is envisioned that the switch 80 may be implemented via a variety of embodiments known to those skilled in the art, such as a push button switch being disposed on the fixed handle 65 and being activated by physical contact of the movable handle 60 as the movable handle 60 is actuated. As discussed above, the spring 132 biases the movable handle 60 away from the fixed handle 65 to maintain the switch 80 in an open position thereby preventing inadvertent activation of the DC motor 144. More specifically, the spring 132 biases the coupling member 90 by acting on a housing potion 12a and supporting wall 130.

The DC motor 144 is coupled to a unidirectional clutch 146 which interfaces with a pinion gear 148. Once the DC motor 144 is activated by pulling of the movable handle 60, the clutch 146 rotates in a clockwise direction rotating the gear 148 in the clockwise direction as well. The gear 148 interfaces with a rack surface 95 of the coupling member 90 and the rotational motion of the gear 148 translates the coupling member 90 in a longitudinal motion, advancing the coupling member 90 and the firing rod 55 in a distal direction "D."

The rate at which the DC motor 144 rotates, and hence, the rate at which the firing shaft 55 is moved in the distal direction, is controlled via the variable resistor 140. In FIG. 1 the variable resistor 140 is shown as a potentiometer 141 with a contact 143 (e.g., wiper terminal) disposed in contact therewith. The contact 143 is coupled to the shaft connector 92 via a shaft 134. The contact 143 slides along the surface of the potentiometer 141 as the coupling member 90 is moved in the distal direction by pulling of the movable handle 60. As the contact 143 slides across the potentiometer 141 the voltage supplied to the DC motor 144 varies accordingly. In particular, varying the position of the contact 143 along the potentiometer 141 adjusts the rate of rotation of the DC motor 144. The distance the contact 143 moves along the potentiometer 141 is proportional to the force exerted by the user in pulling the movable handle 60. As the movable handle 60 is moved, contact 143 moves a distance, and the pulling force on the movable handle 60 is counterbalanced by the force of the spring 132 on the movable handle 60. The further the contact 142 moves under the pulling action on the movable handle 60, the more compression force is applied by the spring 132. Consequently, the rate of rotation of the DC motor 144 and the force with which the firing shaft 55 is moved distally is proportional to the pulling force. Namely, when resistance in potentiometer 141 is low, the torque form the DC motor 144 is high and when the resistance in potentiometer 141 is high, the torque from the DM motor 144 is low.

The switch 80 is arranged to allow clamping of tissue before the motor 144 is actuated. This provides for user control of the initial grasping of the tissue with the end effector 100 and subsequent power-assisted firing of surgical fasteners 115. Those skilled in the art will appreciate that the disclosed variable resistor 140 may also be a rheostat.

Use of the surgical stapler 10 is as follows. The surgical stapler is positioned with the end effector 100 at the surgical site and the tissue engaging surfaces 110 and 120 are placed around tissue. The user thereafter initiates the stapling process by pulling on the movable handle 60 to bring the movable handle 60 toward the fixed handle 65 and clamp tissue. With further movement of movable handle 60, the switch 80 is closed. Simultaneously, the movable handle 60 moves the coupling member 90 in the distal direction along the direction "C" thereby moving the contact 143 along the potentiometer 141. The clamping force exerted by the pulling of the movable handle 60 is counterbalanced by the tissue being grasped and the spring 132. As the movable handle 60 moves the coupling member 90, the contact 143 moves along the potentiometer 141, adjusting the voltage supplied to the DC motor 144. The DC motor 144 rotates at the rate corresponding to the supplied voltage as varied by the variable resistor 140. In response thereto, the DC motor 144 actuates the pinion gear 148 via the unidirectional clutch 146. The rotational motion of the pinion gear 148, which interfaces with the rack surface 95, is translated into longitudinal motion of the coupling member 90 and the firing shaft 55. The firing shaft 55 forces the staple firing mechanism 70 and knife assembly 75 through tissue to sequentially fasten and separate the tissue. Consequently, the rates at which the opposing tissue contacting surfaces 110 and 120 are closed and the staples are fired are directly proportional to the pulling force on the movable handle 60. This provides the user with tactile feedback during the stapling process. Those skilled in the art will appreciate that a series of gears, shafts, screws or other mechanisms may be employed to convert the rotational energy of the drive assembly 20 to firing shaft 55 to actuate tool assembly 100. The drive assembly 20 desirably includes a switch for reversing the motor 144 for retracting the staple firing mechanism 70, and releasing the end effector 100 from tissue. A button may be provided on the housing 12 to actuate the switch.

FIG. 3 shows another embodiment of the surgical stapler 10 which utilizes the potentiometer 141 as a switch to activate the drive assembly 20. In this embodiment, switch 80 and hence contacts 81, 82 are not used. When the movable handle 60 is in the open position away from the fixed handle 65, the potentiometer 141 does not electrically contact the contact 143. When the movable handle 60 is brought toward the fixed handle 65 to clamp tissue, the potentiometer 141 is brought into contact with the contact 143 and the drive assembly 20 is activated. The drive assembly 20 is controlled by varying the voltage as the potentiometer 141 is sliding across the contact 143, which corresponds to the clamp force being applied to the movable handle 60.

Figure 4:
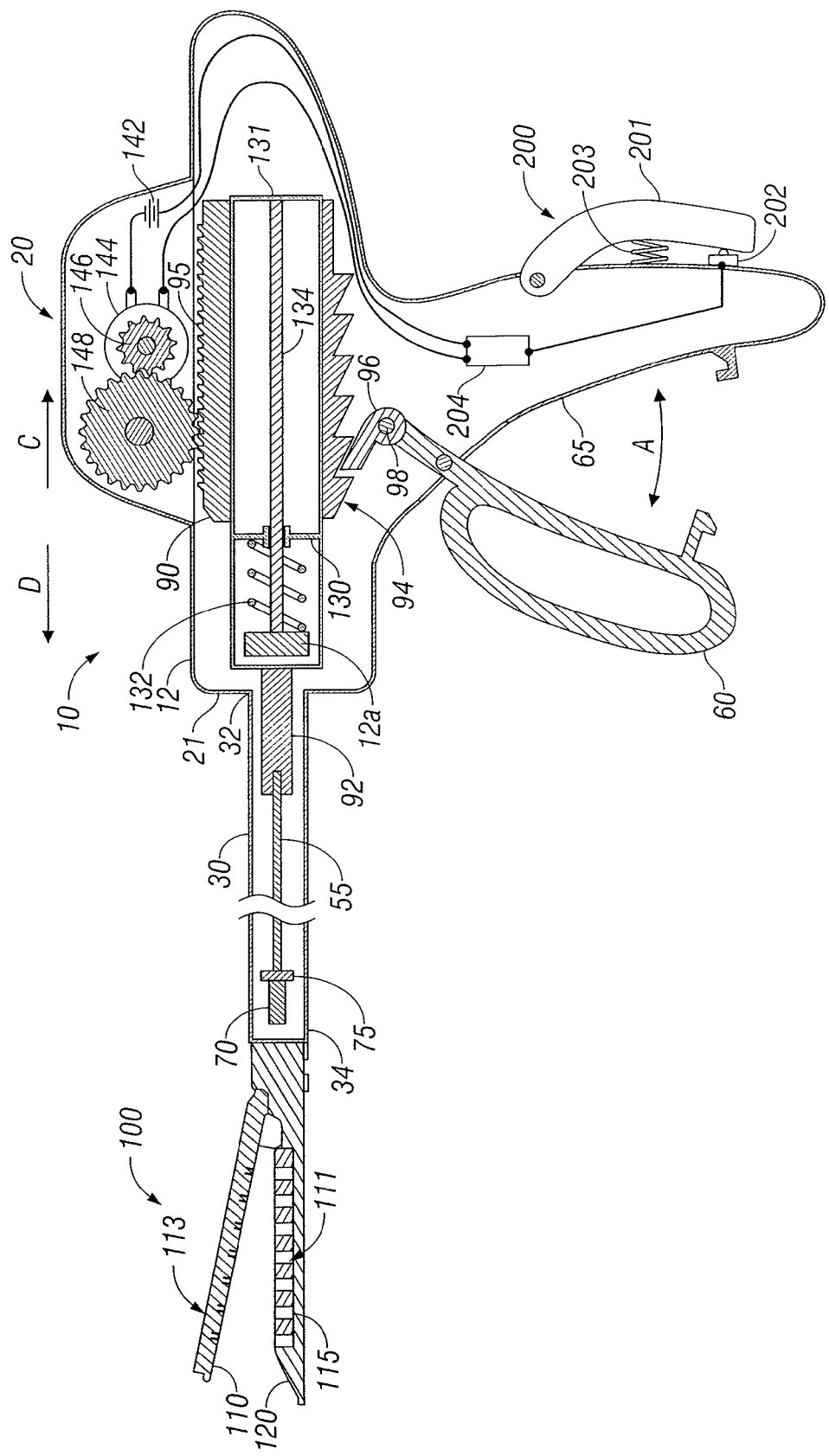
FIG. 4 is a schematic, side view with portions broken away of a surgical stapler according to another embodiment of the present disclosure.

FIG. 4 shows a further embodiment of the surgical stapler 10 having a switch assembly 200. The switch assembly 200 is used in place of the potentiometer 141, contact 143 and the switch 80. The switch assembly 200 includes a handle 201 which is pivotally coupled to the fixed handle 65. The handle 201 is biased by a spring 203 against the fixed handle 65. The switch assembly 200 also includes a pressure sensor 202 disposed between the fixed handle 65 and the handle 201. The pressure sensor 201 may be a piezoelectric sensor configured to sense pressure applied by the handle 201. During clamping, as the movable handle 60 is pulled toward the fixed handle 65, the handle 201 is pushed toward the fixed handle 65. The pressure sensor 202 records pressure applied on the handle 201 as sensor signals, which are representative of the clamping force, and transmits the signals to a motor controller 204. The motor controller 204 thereafter controls the drive assembly 20 based on the sensor signals. The rates at which the opposing tissue contacting surfaces 110 and 120 are closed and the staples are fired are directly proportional to the pushing force on the handle 201.

Preferably, the presently disclosed staplers are designed for endoscopic use and are dimensioned to fit through a trocar or cannula for various endoscopic and laparoscopic procedures. As can be appreciated, the overall dimensions of the tool assembly and the elongated shaft are sized accordingly to fit through the trocar or cannula. Alternatively, the presently disclosed staplers may also be designed and/or used for open surgical procedures. The disclosed surgical staplers preferably are suitable for one-handed operation by the user.

The surgical stapler of FIG. 1 has a staple firing mechanism 70 that deploys staples from the staple cartridge assembly, as well as engages the cartridge assembly and anvil assembly to clamp tissue therebetween. It is contemplated that separate clamping and firing mechanisms may be used. By way of example, the anvil assembly and cartridge assembly may be approximated using a tube that is separate from the staple firing mechanism, as disclosed in U.S. Pat. No. 5,318,221, the disclosure of which is hereby incorporated by reference herein.

It will be understood that various modifications may be made to the embodiments shown herein. Therefore, the above description should not be construed as limiting, but merely as exemplifications of preferred embodiments. Those skilled in the art will envision other modifications within the scope and spirit of the claims appended hereto.

The invention claimed is:
1. A medical instrument, comprising:
a housing having a fixed handle;
a movable handle operably connected to the housing and movable relative to the fixed handle;
an elongated member including at least a fastener firing assembly, the elongated member having a distal end and a proximal end;
a drive assembly including at least a motor and operably coupled to the proximal end of the elongated member;
an end effector operably coupled to the distal end of the elongated member; and a switch assembly mounted to the fixed handle, the switch assembly including a switch handle pivotally coupled to the fixed handle, the switch handle being biased by a spring disposed between the switch handle and the fixed handle;

wherein the motor is configured to be actuated by a controller to variably control a rate at which the motor actuates the end effector and a rate at which the motor is actuated is variably controlled in response to longitudinal motion applied to the fastener firing assembly.

2. The medical instrument according to claim 1, wherein the drive assembly further includes a power source operatively connected to the motor.

3. The medical instrument according to claim 1, wherein the movable handle is selectively movable relative to the fixed handle from a first position in spaced relation relative to the fixed handle to a second position closer to the fixed handle to facilitate clamping of tissue via the end effector.

4. The medical instrument according to claim 1, wherein the fastener firing assembly includes a firing shaft and the end effector includes a plurality of fasteners loaded therein; and wherein the motor actuates a coupling member to advance the firing shaft of the fastener firing assembly to deploy and deform the plurality of fasteners disposed within the end effector.

5. The medical instrument according to claim 1, wherein the switch assembly further includes a pressure sensor disposed between the switch handle and the fixed handle.

6. The medical instrument according to claim 5, wherein the pressure sensor is a piezoelectric sensor configured to sense pressure applied by the switch handle.

7. The medical instrument according to claim 5, wherein the pressure sensor records pressure applied on the switch handle as sensor signals, the sensor signals being representative of a clamping force.

8. The medical instrument according to claim 7, wherein the sensor signals are transmitted to a motor controller disposed within the fixed handle.

9. The medical instrument according to claim 1, wherein the end effector includes a pair of opposing jaw members, the first jaw member including an anvil assembly and the second jaw member including a cartridge assembly having a plurality of fasteners, the pair of opposing jaw members actuated by the motor.

10. A medical instrument, comprising:
a housing having a fixed handle;
a movable handle operably connected to the housing and movable relative to the fixed handle;
an elongated member including a fastener firing assembly having a firing shaft and a knife assembly, the elongated member having a distal end and a proximal end;
a drive assembly including a power source and a motor operably coupled to the proximal end of the elongated member, the motor configured to be actuated by a controller that variably control a rate at which the motor actuates an end effector of the medical instrument;
an end effector operably coupled to the distal end of the elongated member, the end effector including a pair of opposing jaw members, the first jaw member including an anvil assembly and the second jaw member including a cartridge assembly having a plurality of fasteners, the pair of opposing jaw members being actuated by the motor;
a switch assembly mounted to the fixed handle, the switch assembly including a switch handle pivotally coupled to the fixed handle, the switch handle being biased by a spring disposed between the switch handle and the fixed handle; and
a controller operatively associated with the motor to variably control a rate at which the motor actuates the end effector, where a rate at which the motor is actuated is variably controlled in response to a longitudinal motion applied to the fastener firing assembly.

11. The medical instrument according to claim 10, wherein the drive assembly further includes a power source operatively connected to the motor.

12. The medical instrument according to claim 10, wherein the movable handle is selectively movable relative to the fixed handle from a first position in spaced relation relative to the fixed handle to a second position closer to the fixed handle to facilitate clamping of tissue via the end effector.

13. The medical instrument according to claim 10, wherein the motor actuates a coupling member adapted for advancing a firing shaft of the fastener firing assembly to deploy and deform a plurality of fasteners disposed within the end effector.

14. The medical instrument according to claim 10, wherein the switch assembly further includes a pressure sensor disposed between the switch handle and the fixed handle.

15. The medical instrument according to claim 14,
wherein the pressure sensor records pressure applied on the switch handle as sensor signals, the sensor signals being representative of a clamping force; and
wherein the sensor signals are transmitted to a motor controller disposed within the fixed handle.

16. The medical instrument according to claim 14, wherein the pressure sensor is a piezoelectric sensor configured to sense pressure applied by the switch handle.

* * * * *